(12) United States Patent
Shirai (10) Patent No.: US 11,219,377 B2
(45) Date of Patent: Jan. 11, 2022

(54) MEASURING INSTRUMENT AND MEASURING SYSTEM

(71) Applicant: RENESAS ELECTRONICS CORPORATION, Tokyo (JP)

(72) Inventor: Yasuhiro Shirai, Tokyo (JP)

(73) Assignee: RENESAS ELECTRONICS CORPORATION, Tokyo (JP)

(*) Notice: Subject to any disclaimer, the term of this patent is extended or adjusted under 35 U.S.C. 154(b) by 362 days.

(21) Appl. No.: 16/286,410

(22) Filed: Feb. 26, 2019

(65) Prior Publication Data
US 2019/0298189 A1    Oct. 3, 2019

(30) Foreign Application Priority Data
Mar. 27, 2018 (JP) .............................. JP2018-059313

(51) Int. Cl.
*A61B 5/021* (2006.01)
*G01H 5/00* (2006.01)
*G01H 11/08* (2006.01)
*A61B 5/00* (2006.01)

(52) U.S. Cl.
CPC .......... *A61B 5/02108* (2013.01); *A61B 5/681* (2013.01); *A61B 5/7221* (2013.01); *A61B 5/742* (2013.01); *G01H 5/00* (2013.01); *G01H 11/08* (2013.01); *A61B 2562/0219* (2013.01)

(58) Field of Classification Search
CPC ... A61B 5/02108; A61B 5/7221; A61B 5/742; A61B 5/681; A61B 2562/0219; A61B 2562/0247; A61B 5/02125; G01H 5/00; G01H 11/08
See application file for complete search history.

(56) References Cited

U.S. PATENT DOCUMENTS

| 5,241,964 A | * | 9/1993 | McQuilkin | ........ A61B 5/02125 600/485 |
| 5,494,043 A | * | 2/1996 | O'Sullivan | ........ A61B 5/02208 600/500 |
| 2017/0143216 A1 | * | 5/2017 | Oksala | ................ A61B 5/02422 |
| 2017/0319146 A1 | * | 11/2017 | Park | .................... A61B 5/02116 |

FOREIGN PATENT DOCUMENTS

JP            2011-050546 A          3/2011

* cited by examiner

*Primary Examiner* — Devin B Henson
*Assistant Examiner* — Joseph A Tombers
(74) *Attorney, Agent, or Firm* — McDermott Will & Emery LLP

(57) ABSTRACT

A measuring device and measuring system which accurately measure a pulse wave propagation velocity. The measuring instrument includes: a fixing part attachable to and detachable from a subject; a first piezoelectric sensor fixed to the fixing part; a second piezoelectric sensor fixed to the fixing part at a prescribed distance from the first piezoelectric sensor; and an analyzing part for calculating a pulse wave propagation velocity in the subject according to time difference between time of detection of peak voltage by the first piezoelectric sensor and time of detection of peak voltage by the second piezoelectric sensor, and the prescribed distance.

20 Claims, 6 Drawing Sheets

MEASURING INSTRUMENT AND MEASURING SYSTEM

CROSS-REFERENCE TO RELATED APPLICATIONS

The disclosure of Japanese Patent Application No. 2018-059313 filed on Mar. 27, 2018 including the specification, drawings and abstract is incorporated herein by reference in its entirety.

BACKGROUND

The present invention relates to a measuring instrument and a measuring system and more particularly to a measuring instrument and measuring system suitable for measuring the propagation velocity of vibration propagated from a source of vibration accurately.

Japanese Unexamined Patent Application Publication No. 2011-50546 discloses a measuring instrument which measures the artery propagation velocity of a subject. The measuring instrument includes a first thin-film piezoelectric sensor for detecting the pulse pressure waveform on an artery in the wrist of the subject; a second thin-film piezoelectric sensor for detecting the pulse pressure waveform on an artery in the ankle of the subject; a recording device for recording detected values from the first and second thin-film piezoelectric sensors together with sampling times; and an analyzer. The analyzer analyzes and evaluates the artery propagation velocity per passage time according to the sampling time difference between peak detected values for the same pulse pressure as detected by the first and second thin-film piezoelectric sensors respectively, and the difference between the direct distance from the chest to the wrist and the direct distance from the chest to the ankle.

SUMMARY

However, the technique disclosed in Japanese Unexamined Patent Application Publication No. 2011-50546 has a problem that the artery propagation velocity cannot be measured accurately because the difference between the direct distance from the chest to the first thin-film piezoelectric sensor attached to the wrist and the direct distance from the chest to the second thin-film piezoelectric sensor attached to the ankle is not accurate. Therefore, an object of the present invention is to solve the problem. The above and further objects and novel features of the invention will more fully appear from the following detailed description in this specification and the accompanying drawings.

According to one aspect of the present invention, there is provided a measuring instrument which includes: a fixing part attachable to and detachable from a subject; a first piezoelectric sensor fixed to the fixing part; a second piezoelectric sensor fixed to the fixing part at a prescribed distance from the first piezoelectric sensor; and an analyzing part for calculating a propagation velocity of vibration propagated from a source of vibration of the subject according to time difference between times of detection of peak voltages by the first piezoelectric sensor and the second piezoelectric sensor respectively, and the prescribed distance.

According to a second aspect of the invention, there is provided a measuring system which includes: a plurality of measuring instruments attachable to and detachable from a subject for measuring a relative value of propagation velocity of vibration propagated from a source of vibration of the subject; and a decision device for making a comparison of measurement results of the measuring instruments and deciding whether any of the measurement results is abnormal or not, according to a result of the comparison. In the measuring system, each of the measuring instruments includes: a fixing part attachable to and detachable from the subject; a first piezoelectric sensor fixed to the fixing part; a second piezoelectric sensor fixed to the fixing part at a prescribed distance from the first piezoelectric sensor; and an analyzing part for calculating a relative value of propagation velocity of vibration propagated from the source of vibration of the subject according to time difference between time of detection of peak voltage by the first piezoelectric sensor and time of detection of peak voltage by the second piezoelectric sensor.

According to a third aspect of the invention, there is provided a measuring instrument which includes: a fixing part attachable to and detachable from a subject; a first piezoelectric sensor fixed to the fixing part; a second piezoelectric sensor fixed to the fixing part at a prescribed distance from the first piezoelectric sensor; and an analyzing part for calculating a propagation velocity of vibration propagated from a source of vibration of the subject according to time difference between times of detection of voltages for a vibration by the first piezoelectric sensor and the second piezoelectric sensor respectively, and the prescribed distance.

According to the present invention, there are provided a measuring instrument and a measuring system which can accurately measure the propagation velocity of vibration propagated from a source of vibration.

DETAILED DESCRIPTION

In order to clarify the description, the explanations and drawings given hereinafter are briefed and simplified as appropriate. The elements illustrated in drawings as functional blocks for performing various types of processing may be comprised of a CPU (Central Processing Unit), memory, and other circuits in terms of hardware and may be implemented by a program loaded in a memory or the like in terms of software. Therefore, it is understood by those skilled in the art that these functional blocks can be implemented in various forms by only hardware, only software or a combination of hardware and software, and the way how the functional blocks are implemented is not limited to a given form. In the drawings, the same elements are designated by the same reference signs and their repeated description is omitted as necessary.

The above program can be stored in many types of non-transitory computer-readable media and supplied to a computer. The non-transitory computer-readable media include many types of substantial recording media. Among examples of the non-transitory computer-readable media are a magnetic recording medium (for example, flexible disk, magnetic tape, hard disk drive), magneto optical recording medium (for example, magneto optical disk), CD-ROM (Read Only Memory), CD-R, CD-R/W, and semiconductor memory (for example, mask ROM, PROM (Programmable ROM), EPROM (Erasable PROM), flash ROM, and RAM (Random Access Memory)). The program may be supplied to a computer by many types of non-transitory computer-readable media. Among examples of the non-transitory computer-readable media are electric signals, optical signals, and electromagnetic waves. The non-transitory computer-readable media can supply the program to a computer via a wire communication channel such as an electric wire or optical fiber or a wireless communication channel.

First Embodiment

Figure 1:
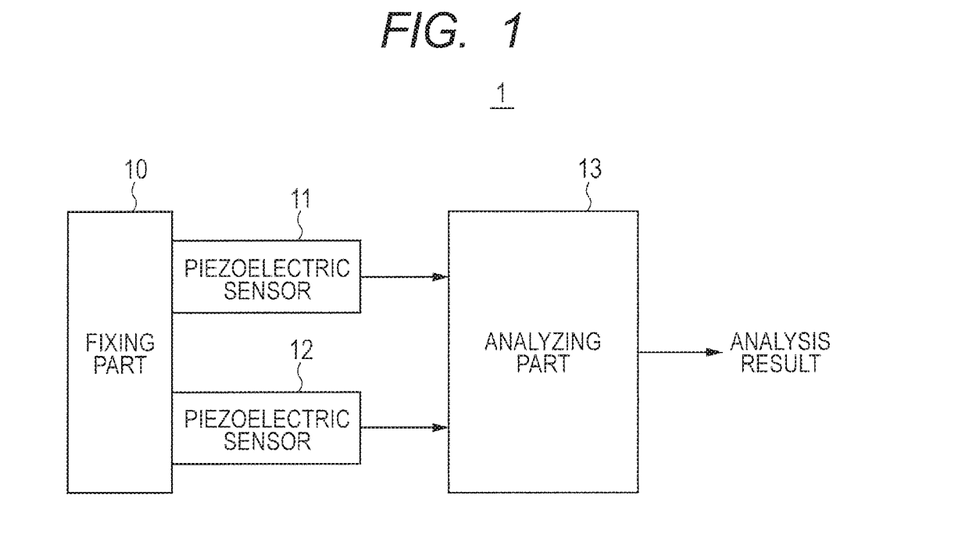
FIG. 1 is a block diagram which shows an example of the configuration of the measuring instrument according to a first embodiment of the invention.

FIG. 1 is a block diagram which shows an example of the configuration of the measuring instrument 1 according to the first embodiment.

The measuring instrument 1 according to this embodiment is a device which measures the propagation velocity of pulse wave propagated from the heart of a subject (animal including a human being) and includes a fixing part 10, piezoelectric sensor 11, piezoelectric sensor 12, and analyzing part (analyzer) 13. In the measuring instrument 1, with the piezoelectric sensors 11 and 12 fixed to the fixing part 10, the analyzing part 13 measures the pulse wave propagation velocity according to the time difference between times of detection of peak voltages by the piezoelectric sensors 11 and 12 respectively and the distance between the piezoelectric sensors 11 and 12. Thus, the distance between the piezoelectric sensors 11 and 12 can be predetermined, so the pulse wave propagation velocity can be measured accurately. Next, an explanation will be given in detail referring to FIGS. 2 to 4.

Figure 2:
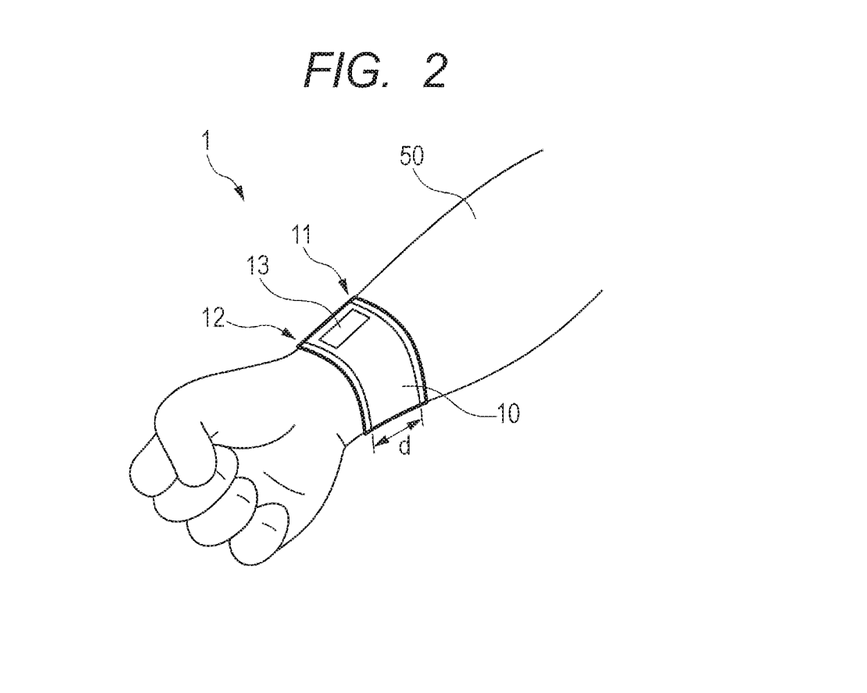
FIG. 2 shows an example of the measuring instrument shown in FIG. 1 which is attached to a subject.

FIG. 2 shows an example of the measuring instrument 1 attached to a subject 50.

As shown in FIG. 2, the fixing part 10 is attachable to and detachable from a wrist or ankle of the subject 50. For example, the fixing part 10 has the shape of an expandable cylinder. In the example shown in FIG. 2, the fixing part 10 is a wrist band.

The piezoelectric sensors 11 and 12 output the detected voltages V1 and V2 of values corresponding to the pressures of pulse waves propagated from the heart of the subject 50, respectively. The piezoelectric sensors 11 and 12 are, for example, formed to be circular along the side faces of the cylindrical fixing part 10. The piezoelectric sensors 11 and 12 are fixed to the fixing part 10 with a prescribed distance d between them.

The analyzing part 13 measures time difference ΔT between the time of detection of an arbitrary voltage VP1 among the voltages V1 detected by the piezoelectric sensor 11 and the time of detection of voltage VP2 for the same pulse wave as the voltage VP1, among the voltages V2 detected by the piezoelectric sensor 12.

Figure 3:
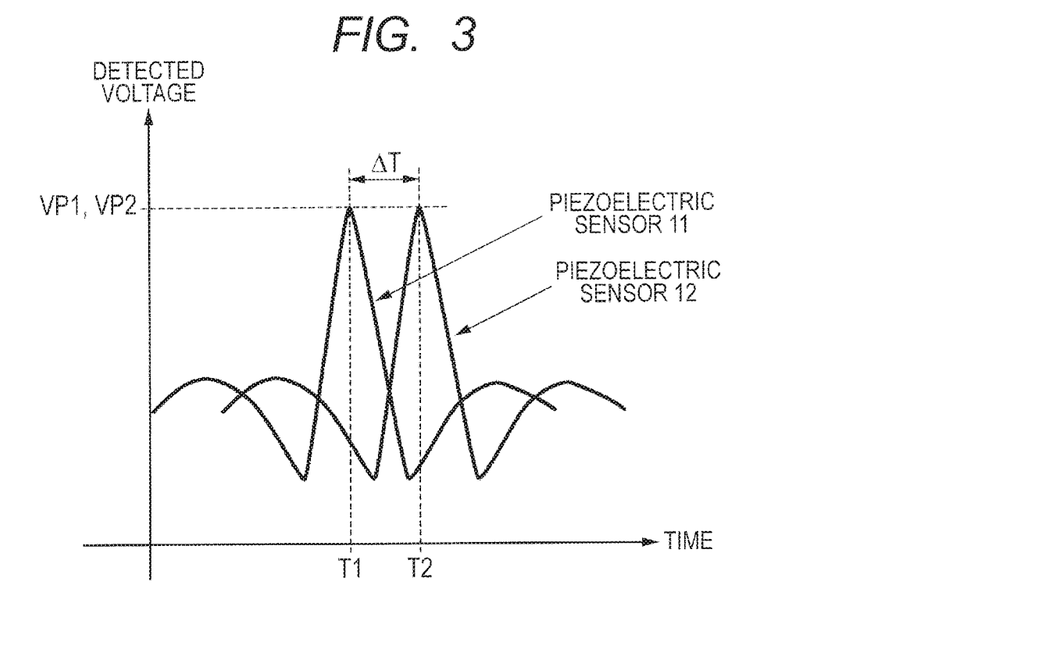
FIG. 3 shows an example of the waveforms of voltages detected by the piezoelectric sensors 11 and 12, respectively.
Figure 4:
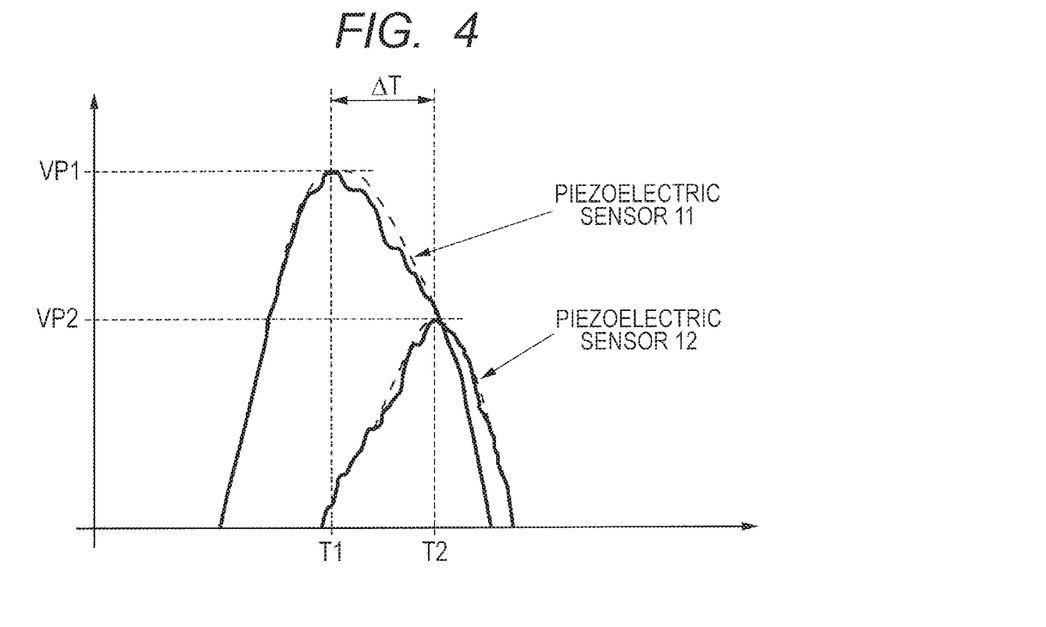
FIG. 4 shows another example of the waveforms of voltages detected by the piezoelectric sensors 11 and 12.

FIG. 3 shows the waveforms of voltages V1 and V2 detected by the piezoelectric sensors 11 and 12, respectively. FIG. 4 shows details of the waveforms of voltages V1 and V2 detected by the piezoelectric sensors 11 and 12.

As shown in FIG. 3, the analyzing part 13 measures time difference ΔT between time T1 of detection of peak voltage VP1 among the voltages V1 detected by the piezoelectric sensor 11 and time T2 of detection of peak voltage VP2 among the voltages V2 detected by the piezoelectric sensor 12. As shown in FIG. 4, peak voltages VP1 and VP2 may be identified from the waveforms (broken lines) of detected voltages after correction using an approximate equation such as a quadratic function.

After that, the analyzing part 13 measures the pulse wave propagation velocity (PWV) by dividing the prescribed distance d by time difference ΔT. Since the prescribed distance d is fixed, the analyzing part 13 can measure the pulse wave propagation velocity accurately.

For example, when the prescribed distance d is fixed at 5 cm, if time difference ΔT is approximately 3.1 msec or less, the pulse wave propagation velocity exceeds 1600 cm/sec and it is thus decided that there is the risk of arterial sclerosis.

As explained above, in the measuring instrument 1 according to this embodiment, with the piezoelectric sensors 11 and 12 fixed to the fixing part 10, the analyzing part 13 measures the pulse wave propagation velocity according to time difference ΔT between times T1 and T2 of detection of peak voltages VP1 and VP2 by the piezoelectric sensors 11 and 12 respectively and the prescribed distance d between the piezoelectric sensors 11 and 12. Since the distance between the piezoelectric sensors 11 and 12 can be predetermined, the pulse wave propagation velocity can be measured accurately.

Furthermore, unlike the measuring instrument disclosed in Japanese Unexamined Patent Publication No. 2011-50546, in the measuring instrument 1 according to this embodiment, the piezoelectric sensors 11 and 12 need not be attached to different limbs among the four limbs and the piezoelectric sensors 11 and 12 can be attached to the same limb (for example, right wrist), so the pulse wave propagation velocity can be locally measured.

Variation of the Measuring Instrument 1

Figure 5:
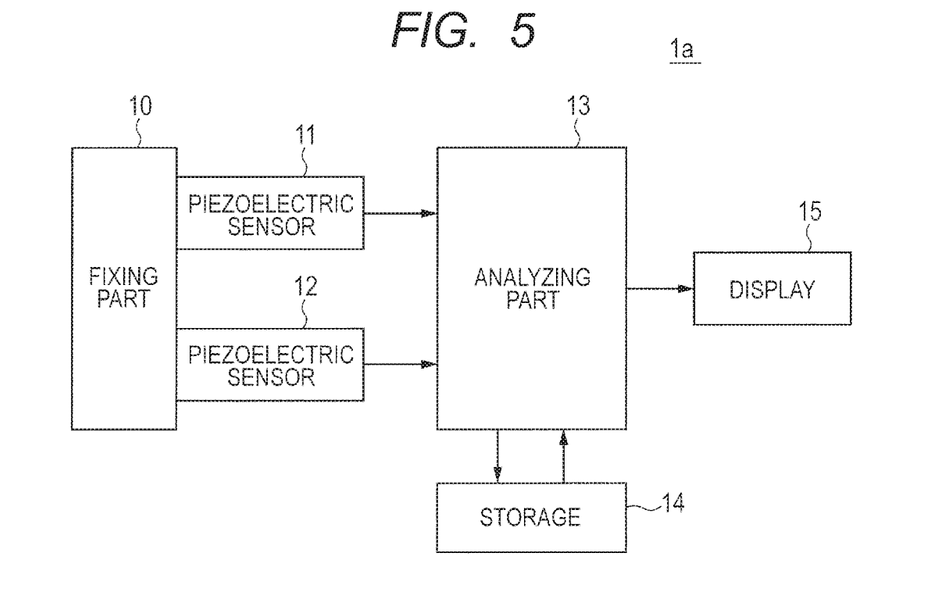
FIG. 5 is a block diagram which shows a measuring instrument as a variation of the measuring instrument shown in FIG. 1.

FIG. 5 is a block diagram which shows a measuring instrument 1a as a variation of the measuring instrument 1.

As shown in FIG. 5, the measuring instrument 1a further includes a storage (storage device) 14 and a display (display device) 15, as compared with the measuring instrument 1.

The storage 14 stores the result of analysis by the analyzing part 13 (measurement result). The storage 14 may be built in the measuring instrument 1a or detachable like an SD card or the like. The analyzing part 13 reads the analysis result stored in the storage 14 and displays it on the screen of the display 15. The display 15 may be fitted to the front surface of the measuring instrument 1a or may be an external device which can make communication, such as a smart phone or personal computer. If the display 15 is an external device which can make communication, such as a smart phone or personal computer, the measuring instrument 1a may be structured to start or end measurement of pulse wave according to control from the external device.

(Example of the Configuration of a Measuring System Using a Plurality of Measuring Instruments 1)

Figure 6:
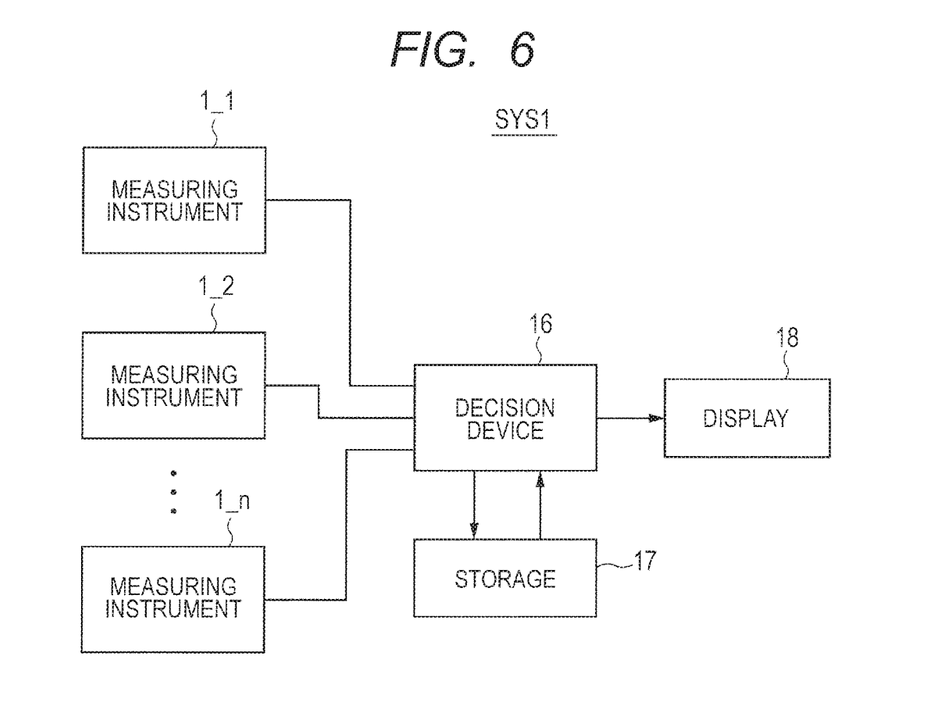
FIG. 6 is a block diagram which shows an example of the configuration of a measuring system using the measuring instrument shown in FIG. 1.

FIG. 6 is a block diagram which shows an example of the configuration of a measuring system SYS1 using a plurality of measuring instruments 1. As shown in FIG. 6, the measuring system SYS1 includes a plurality of measuring instruments 1, a decision device 16, a storage (storage device) 17, and a display (display device) 18. In description of this embodiment, the measuring system SYS1 is assumed to include four measuring instruments 1 (hereinafter called measuring instruments 1_1 to 1_4).

The measuring instrument 1_1 is attached, for example, to the right wrist among the four limbs of the subject 50. The measuring instrument 1_2 is attached, for example, to the left wrist among the four limbs of the subject 50. The measuring instrument 1_3 is attached, for example, to the right ankle among the four limbs of the subject 50. The measuring instrument 1_4 is attached, for example, to the left ankle among the four limbs of the subject 50.

The decision device 16 decides whether or not the pulse wave of the subject 50 is normal, from the results of measurement by the measuring instruments 1_1 to 1_4. For example, if the results of measurement by the measuring instruments 1_1 to 1_4 are all not more than a reference value, the decision device 16 decides that the pulse wave of the subject 50 is normal and if any one of the results of measurement by the measuring instruments 1_1 to 1_4 is more than the reference value, it decides that the pulse wave of the subject 50 is abnormal.

The storage 17 stores the results of measurement by the measuring instruments 1_1 to 1_4 and stores the result of decision by the decision device 16. The decision device 16 reads the decision result stored in the storage 17 and displays it on the screen of the display 18. Concrete examples of the storage 17 and display 18 are the same as concrete examples of the storage 14 and display 15 and their description is omitted. If the result of decision by the decision device 16 need not be stored in the storage 17, the storage 17 need not be provided. If the result of decision by the decision device 16 need not be displayed on the screen of the display 18 and is sent to an external device by another means, the display 18 need not be provided.

Thus, the measuring system SYS1 can measure the pulse wave propagation velocity locally from each of several regions of the subject 50 and can decide whether or not a region among the several regions of the subject 50 has an abnormal pulse wave (namely, whether or not there is the risk of artery sclerosis).

Even when the accurate value of the prescribed distance d between the piezoelectric sensors 11 and 12 of each of the measuring instruments 1_1 to 1_4 is unknown, the measuring system SYS1 can compare the results of measurement by the measuring instruments 1_1 to 1_4 and if one measurement result is largely different from all the other measurement results, it can decide that the measurement result (pulse wave) concerned is abnormal.

Second Embodiment

Figure 7:
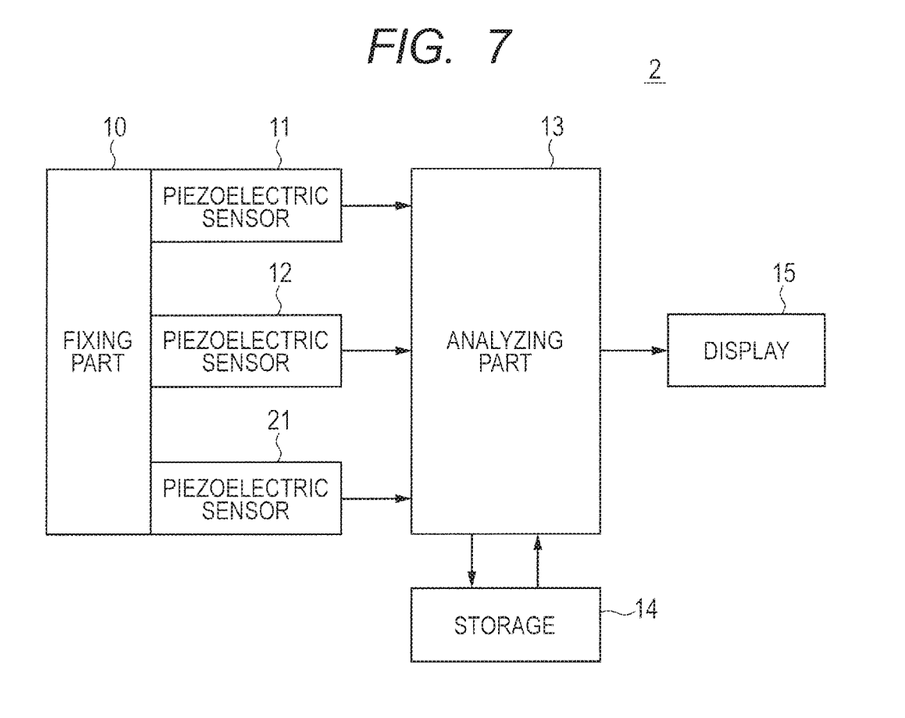
FIG. 7 is a block diagram which shows an example of the configuration of the measuring instrument according to a second embodiment of the invention.

FIG. 7 is a block diagram which shows an example of the configuration of the measuring instrument 2 according to the second embodiment. As shown in FIG. 7, the measuring instrument 2 further includes one or more piezoelectric sensors 21 as compared with the measuring instrument 1a.

The storage 14 stores a table of correction values for electromotive forces outputted from the piezoelectric sensors 21.

The analyzing part 13 first measures the pulse wave propagation velocity according to time difference $\Delta T$ between times T1 and T2 of detection of peak voltages VP1 and VP2 by the piezoelectric sensors 11 and 12 respectively and the prescribed distance d between the piezoelectric sensors 11 and 12. Further, the analyzing part 13 extracts a correction value (correction values) for an electromotive force (electromotive forces) outputted from one or more piezoelectric sensors 21, from the table stored in the storage 14 and corrects the pulse wave propagation velocity by the extracted correction value.

Figure 8:
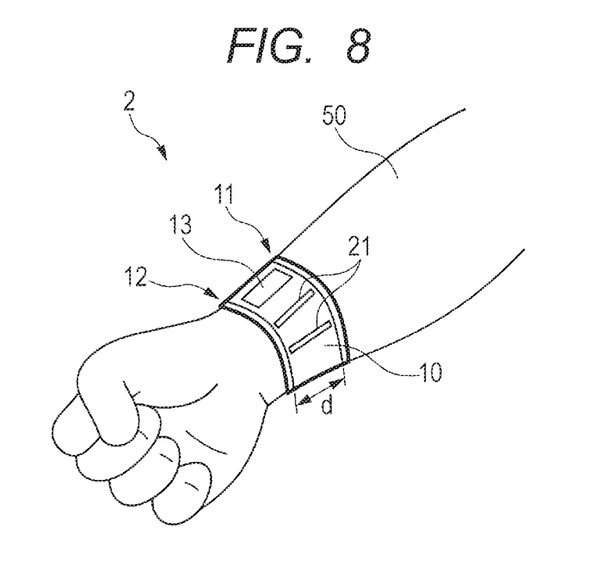
FIG. 8 shows an example of the measuring instrument shown in FIG. 7, which is attached to the subject.

FIG. 8 shows an example of the measuring instrument 2 attached to the subject 50.

In the example shown in FIG. 8, the piezoelectric sensors 21 are arranged between the piezoelectric sensors 11 and 12 and electrically isolated from the piezoelectric sensors 11 and 12. As the fixing part 10 is deformed, each piezoelectric sensor 21 is deformed, generating an electromotive force depending on the amount of deformation. In other words, each piezoelectric sensor 21 generates an electromotive force depending on the amount of change in the prescribed distance d which changes with the deformation of the fixing part 10. At this time, the analyzing part 13 extracts a correction value for an electromotive force outputted from each piezoelectric sensor 21, from the table stored in the storage 14 and corrects the pulse wave propagation velocity and corrects the pulse wave propagation velocity by the extracted correction value.

Thus, even when the prescribed distance d between the piezoelectric sensors 11 and 12 changes, the measuring instrument 2 according to the second embodiment can detect the amount of change in the prescribed distance d using one or more piezoelectric sensors 21 and thereby accurately correct a pulse wave propagation velocity error caused by the change in the prescribed distance d.

Third Embodiment

Figure 9:
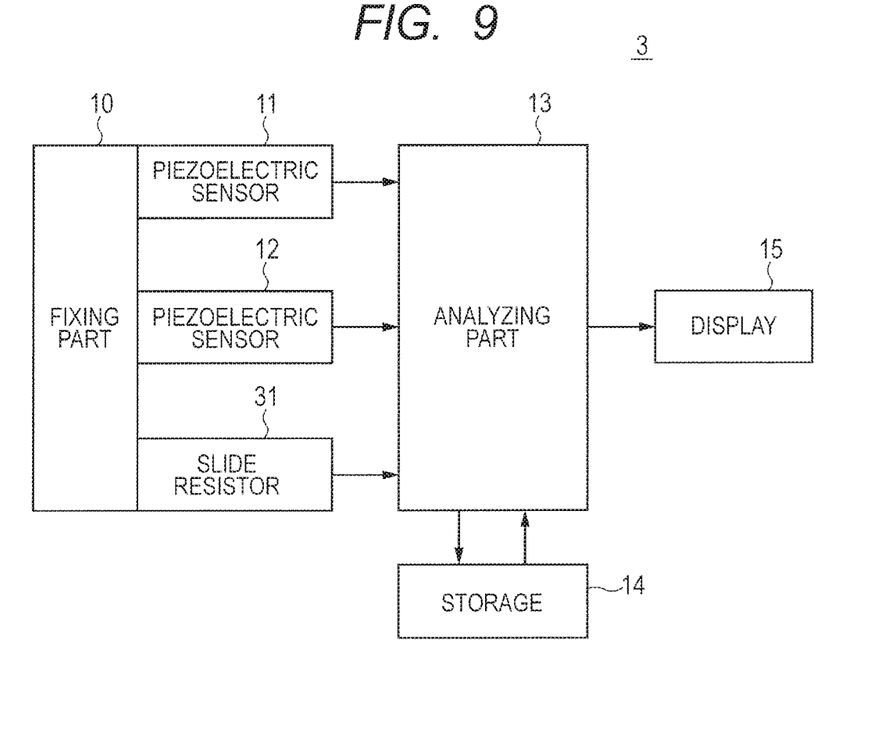
FIG. 9 is a block diagram which shows an example of the configuration of the measuring instrument according to a third embodiment of the invention.

FIG. 9 is a block diagram which shows an example of the configuration of the measuring instrument 3 according to the third embodiment. As shown in FIG. 9, the measuring instrument 3 includes one or more slide resistors 31 in place of one or more piezoelectric sensors 21 as compared with the measuring instrument 2. Also, the storage 14 stores a table of correction values for resistance values of the slide resistor(s) 31.

The analyzing part 13 first measures the pulse wave propagation velocity according to time difference $\Delta T$ between times T1 and T2 of detection of peak voltages VP1 and VP2 by the piezoelectric sensors 11 and 12 respectively and the prescribed distance d between the piezoelectric sensors 11 and 12. Further, the analyzing part 13 extracts a correction value (correction values) for a resistance value (resistance values) of one or more slide resistors 31, from the table stored in the storage 14 and corrects the pulse wave propagation velocity by the extracted correction value.

Figure 10:
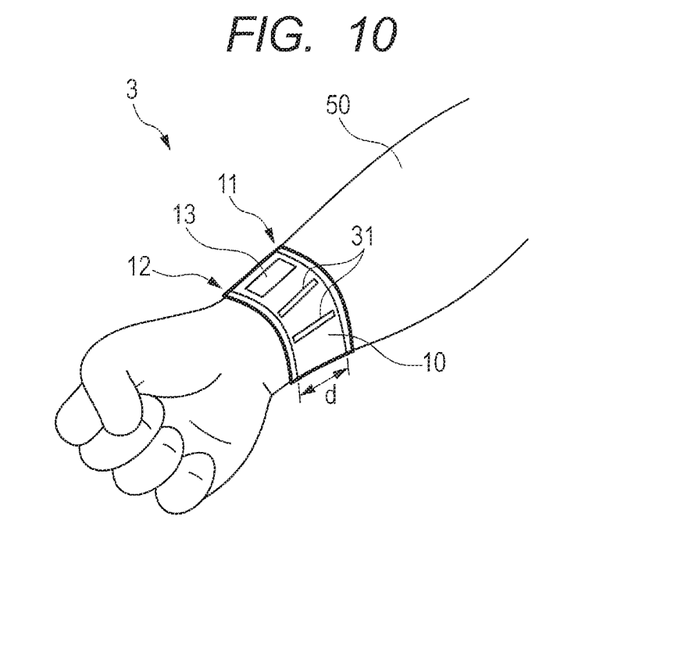
FIG. 10 shows an example of the measuring instrument shown in FIG. 9, which is attached to the subject.

FIG. 10 shows an example of the measuring instrument 3 attached to the subject 50.

In the example shown in FIG. 10, the slide resistors 31 are arranged between the piezoelectric sensors 11 and 12 and electrically isolated from the piezoelectric sensors 11 and 12. As the fixing part 10 is deformed, the resistance value of each slide resistor 31 is changed. In other words, each slide resistor 31 indicates a resistance value depending on the amount of change in the prescribed distance d which changes with the deformation of the fixing part 10. At this time, the analyzing part 13 extracts a correction value for the resistance value of each slide resistor 21, from the table stored in the storage 14 and corrects the pulse wave propagation velocity by the extracted correction value.

Thus, even when the prescribed distance d between the piezoelectric sensors 11 and 12 changes, the measuring instrument 3 according to the third embodiment can detect the amount of change in the prescribed distance d using one or more slide resistors 31 and thereby accurately correct a pulse wave propagation velocity error caused by the change in the prescribed distance d.

Fourth Embodiment

Figure 11:
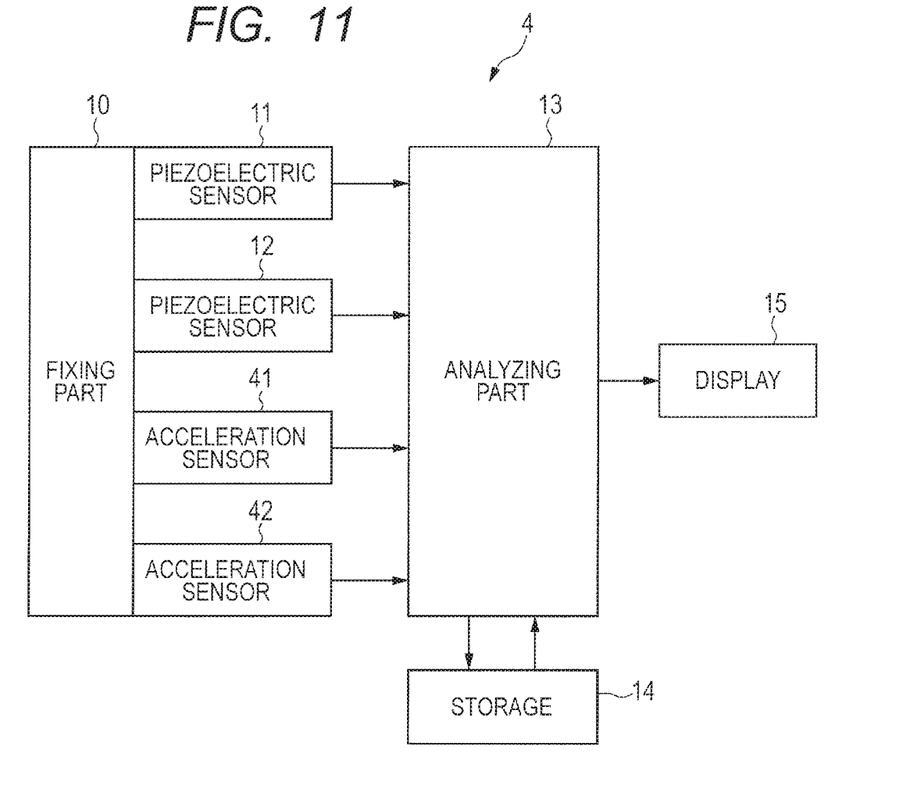
FIG. 11 is a block diagram which shows an example of the configuration of the measuring instrument according to a fourth embodiment of the invention.

FIG. 11 is a block diagram which shows an example of the configuration of the measuring instrument 4 according to the fourth embodiment.

As shown in FIG. 11, the measuring instrument 4 includes two acceleration sensors 41 and 42 in place of one or more piezoelectric sensors 21 as compared with the measuring instrument 2. Also, the storage 14 stores a table of correction values for discrepancies from the prescribed distance d as calculated from the result of time integration of the accelerations of the piezoelectric sensors 11 and 12 as detected by the acceleration sensors 41 and 42.

The analyzing part 13 first measures the pulse wave propagation velocity according to time difference $\Delta T$ between times T1 and T2 of detection of peak voltages VP1 and VP2 by the piezoelectric sensors 11 and 12 respectively and the prescribed distance d between the piezoelectric sensors 11 and 12. Further, the analyzing part 13 identifies the positional relation between the piezoelectric sensors 11 and 12 from the result of time integration of the accelerations of the piezoelectric sensors 11 and 12 as detected by the acceleration sensors 41 and 42 and calculates a discrepancy from the prescribed distance d. Then, the analyzing part 13 extracts a correction value for the calculated discrepancy from the table stored in the storage 14 and corrects the pulse wave propagation velocity by the extracted correction value.

Figure 12:
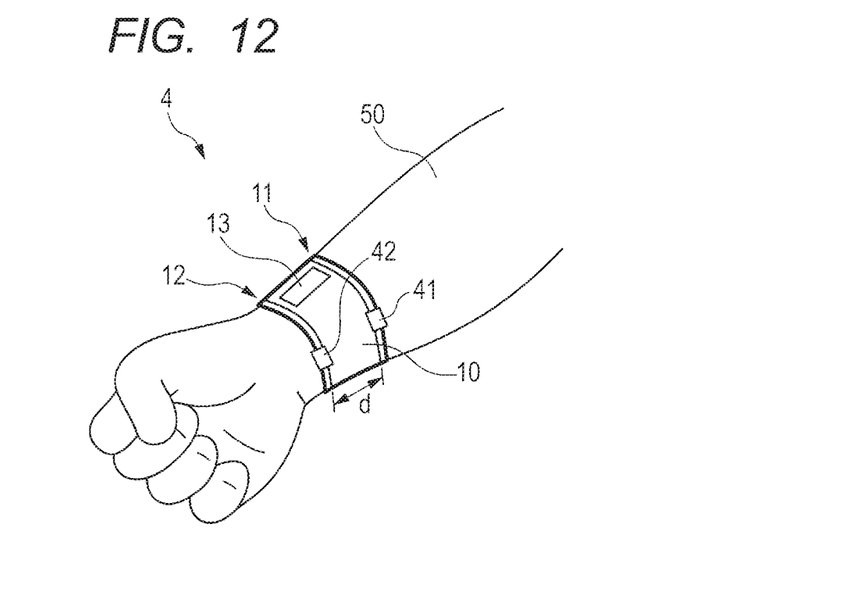
FIG. 12 shows an example of the measuring instrument shown in FIG. 11, which is attached to the subject.

FIG. 12 shows an example of the measuring instrument 4 attached to the subject 50.

In the example shown in FIG. 12, the acceleration sensor 41 is mounted on the piezoelectric sensor 11 and the acceleration sensor 42 is mounted on the piezoelectric sensor 12. When the measuring instrument 4 moves as the subject 50 moves, the acceleration sensors 41 and 42 detect the accelerations of the piezoelectric sensors 11 and 12, respectively. The analyzing part 13 identifies the positional relation between the piezoelectric sensors 11 and 12 from the result of time integration of the accelerations detected by the acceleration sensors 41 and 42 respectively and calculates a discrepancy from the prescribed distance d. Then, the analyzing part 13 extracts a correction value for the calculated discrepancy from the table stored in the storage 14 and corrects the pulse wave propagation velocity by the extracted correction value.

Thus, even when the prescribed distance d between the piezoelectric sensors 11 and 12 changes, the measuring instrument 4 according to the fourth embodiment can detect the amount of change in the prescribed distance d using the acceleration sensors 41 and 42 and thereby accurately correct a pulse wave propagation velocity error caused by the change in the prescribed distance d.

As described so far, in the measuring instruments 1 to 4 according to the first to fourth embodiments, with the piezoelectric sensors 11 and 12 fixed to the fixing part 10, the analyzing part 13 measures the pulse wave propagation velocity according to time difference $\Delta T$ between times T1 and T2 of detection of peak voltages VP1 and VP2 by the piezoelectric sensors 11 and 12 respectively and the prescribed distance d between the piezoelectric sensors 11 and 12. In the measuring instruments 1 to 4, since the distance between the piezoelectric sensors 11 and 12 can be predetermined, the pulse wave propagation velocity can be measured accurately.

Furthermore, unlike the measuring instrument disclosed in Japanese Unexamined Patent Application Publication No. 2011-50546, in the measuring instruments 1 to 4 according to the first to fourth embodiments, the piezoelectric sensors 11 and 12 need not be attached to different limbs among the four limbs and may be attached to one limb among the four limbs (for example, the right wrist), so the pulse wave propagation velocity can be measured locally.

The invention made by the present inventors has been so far explained concretely in reference to the preferred embodiments thereof. However, the invention is not limited thereto and it is obvious that these details may be modified in various ways without departing from the gist thereof.

The first to fourth embodiments have been described above on the assumption that the measuring instruments 1 to 4 measure the propagation velocity of pulse wave propagated from the heart of the subject 50. However, the invention is not limited thereto. The measuring instruments 1 to 4 can measure the propagation velocity of vibration propagated from an arbitrary source of vibration of the subject 50.

The second to fourth embodiments have been described above on the assumption that a correction value to correct a pulse wave propagation velocity error is extracted from the table stored in the storage 14. However, the invention is not limited thereto. Instead, the correction value may be calculated, for example, using a prescribed arithmetic expression.

What is claimed is:

1. A measuring instrument comprising:
a band that is attachable to and detachable from a subject;
a first piezoelectric sensor that is fixed to the band;
a second piezoelectric sensor that is fixed to the band at a prescribed distance from the first piezoelectric sensor; and
an analyzing circuit that calculates a propagation velocity of vibration of the subject according to 1) times when predetermined voltages are detected by the first piezoelectric sensor and the second piezoelectric sensor respectively and 2) the prescribed distance,
wherein the measuring instrument further comprises a third piezoelectric sensor that is electrically isolated from the first piezoelectric sensor and the second piezoelectric sensor,
wherein the third piezoelectric sensor is provided between the first piezoelectric sensor and the second piezoelectric sensor to detect an amount of change in the prescribed distance between the first piezoelectric sensor and the second piezoelectric sensor, and
wherein the analyzing circuit corrects the propagation velocity according to the detected amount of change in the prescribed distance.

2. The measuring instrument according to claim 1, wherein the analyzing circuit calculates the propagation velocity of vibration propagated from a source of vibration of the subject according to 1) time difference between the times when peak voltages are detected by the first piezoelectric sensor and the second piezoelectric sensor respectively and 2) the prescribed distance.

3. The measuring instrument according to claim 2, wherein the analyzing circuit calculates the propagation velocity of pulse wave propagated from a heart of the subject.

4. The measuring instrument according to claim 1,
wherein the third piezoelectric sensor outputs, to the analyzing circuit, an electromotive force that depends on the amount of change in the prescribed distance between the first piezoelectric sensor and the second piezoelectric sensor, and
wherein the analyzing circuit corrects the propagation velocity according to the electromotive force outputted from the third piezoelectric sensor.

5. The measuring instrument according to claim 4, further comprising:
a storage that stores a table of correction values for electromotive forces outputted from the third piezoelectric sensor,
wherein the analyzing circuit corrects the propagation velocity in reference to the table.

6. The measuring instrument according to claim 2, further comprising:
a slide resistor that is provided between the first piezoelectric sensor and the second piezoelectric sensor, with a resistance value changing depending on a distance between the first piezoelectric sensor and the second piezoelectric sensor,
wherein the analyzing circuit corrects the propagation velocity according to the resistance value of the slide resistor.

7. The measuring instrument according to claim 6, further comprising:
a storage that stores a table of correction values for resistance values of the slide resistor,
wherein the analyzing circuit corrects the propagation velocity in reference to the table.

8. The measuring instrument according to claim 2, further comprising:
a first acceleration sensor that is provided for the first piezoelectric sensor; and
a second acceleration sensor that is provided for the second piezoelectric sensor,
wherein the analyzing circuit corrects the propagation velocity according to a result of time integration of accelerations detected by the first acceleration sensor and the second acceleration sensor.

9. The measuring instrument according to claim 8, further comprising:
a storage that stores a table of correction values corresponding to the result of time integration of the accelerations,
wherein the analyzing circuit corrects the propagation velocity in reference to the table.

10. The measuring instrument according to claim 2,
wherein the band is cylindrical,
wherein the first piezoelectric sensor is formed to be circular along a side face of the cylindrical band, and
wherein the second piezoelectric sensor is formed to be circular along a side face of the cylindrical band at the prescribed distance from the first piezoelectric sensor.

11. The measuring instrument according to claim 10, wherein the band comprises a wrist band.

12. The measuring instrument according to claim 2, further comprising a display device that displays a result of calculation by the analyzing circuit.

13. A measuring system comprising:
a plurality of measuring instruments according to claim 2; and
a decision device that decides whether a result of measurement by each of the measuring instruments is abnormal or not.

14. A measuring system comprising:
a plurality of measuring instruments according to claim 2; and
a decision device that makes a comparison of measurement results of the measuring instruments and decides whether any of the measurement results is abnormal or not, according to a result of the comparison.

15. The measuring instrument according to claim 1,
wherein the predetermined voltage detected by the first sensor comprises a voltage of a first vibration of the subject, and
wherein the predetermined voltage detected by the second sensor comprises a voltage of a second vibration of the subject.

16. The measuring instrument according to claim 15, wherein a time difference between the times when the predetermined voltages are detected by the first piezoelectric sensor and the second piezoelectric sensor is equal to or smaller than a period of the first vibration of the subject.

17. The measuring instrument according to claim 16, wherein the period of the vibration of the subject comprises an interval between a time when a predetermined voltage for the first vibration is detected by the first piezoelectric sensor and a time when a voltage for a third vibration next to the first vibration is detected by the first piezoelectric sensor.

18. A measuring system comprising:
a plurality of measuring instruments that is attachable to and detachable from a subject and measures a relative value of propagation velocity of vibration propagated from a source of vibration of the subject; and
a decision device that makes a comparison of measurement results of the measuring instruments and decides whether any of the measurement results is abnormal or not, according to a result of the comparison,
wherein each of the measuring instruments comprises:
a band that is attachable to and detachable from the subject;
a first piezoelectric sensor that is fixed to the band;
a second piezoelectric sensor that is fixed to the band at a prescribed distance from the first piezoelectric sensor; and
an analyzing circuit that calculates a relative value of propagation velocity of vibration of the subject according to times when predetermined voltages are detected by the first piezoelectric sensor and the second piezoelectric sensor respectively, and the prescribed distance,
wherein each of the measuring instruments further comprises a third piezoelectric sensor that is electrically isolated from the first piezoelectric sensor and the second piezoelectric sensor,
wherein the third piezoelectric sensor is provided between the first piezoelectric sensor and the second piezoelectric sensor to detect an amount of change in the prescribed distance between the first piezoelectric sensor and the second piezoelectric sensor, and
wherein the analyzing circuit corrects the propagation velocity according to the detected amount of change in the prescribed distance.

19. A measuring instrument comprising:
a band that is attachable to and detachable from a subject;
a first piezoelectric sensor that is fixed to the band;

a second piezoelectric sensor that is fixed to the band at a prescribed distance from the first piezoelectric sensor; and an analyzing circuit that calculates a propagation velocity of vibration of the subject according to a time when a voltage for a first vibration is detected by the first piezoelectric sensor, a time when a voltage for a second vibration associated with the first vibration is detected by the second piezoelectric sensor, and the prescribed distance, wherein the measuring instrument further comprises a third piezoelectric sensor that is electrically isolated from the first piezoelectric sensor and the second piezoelectric sensor, wherein the third piezoelectric sensor is provided between the first piezoelectric sensor and the second piezoelectric sensor to detect an amount of change in the prescribed distance between the first piezoelectric sensor and the second piezoelectric sensor, and wherein the analyzing circuit corrects the propagation velocity according to the detected amount of change in the prescribed distance.

20. The measuring instrument according to claim 19, wherein the analyzing circuit calculates the propagation velocity of vibration propagated from a source of vibration of the subject according to time difference between the time when peak voltage for the first vibration is detected by the first piezoelectric sensor, the time when peak voltage for the second vibration associated with the first vibration is detected by the second piezoelectric sensor, and the prescribed distance.

* * * * *